US00PP34444P2

(12) United States Plant Patent
Hopmans

(10) Patent No.: US PP34,444 P2
(45) Date of Patent: Jul. 26, 2022

(54) ***HEBE* PLANT NAMED 'HOP102'**

(50) Latin Name: ***Hebe* Comm. ex. Juss.**
Varietal Denomination: 'HOP102'

(71) Applicant: FIRMA E. HOPMANS, Wieringerwerf (NL)

(72) Inventor: Rudolf Johannes Hopmans, Wieringerwerf (NL)

(73) Assignee: FIRMA E. HOPMANS, Wieringerwerf (NL)

( * ) Notice: Subject to any disclaimer, the term of this patent is extended or adjusted under 35 U.S.C. 154(b) by 0 days.

(21) Appl. No.: 17/566,893

(22) Filed: Dec. 31, 2021

Related U.S. Application Data

(60) Provisional application No. 63/133,549, filed on Jan. 4, 2021.

(51) Int. Cl.
*A01H 6/68* (2018.01)
*A01H 5/02* (2018.01)

(52) U.S. Cl.
USPC ..... Plt./251

(58) Field of Classification Search
USPC ..... Plt./251, 226
See application file for complete search history.

(56) References Cited

PUBLICATIONS

CPVO Variety Data Sheet 2021.*

* cited by examiner

*Primary Examiner* — Annette H Para
(74) *Attorney, Agent, or Firm* — C. Anne Whealy

(57) ABSTRACT

A new and distinct cultivar of *Hebe* plant named 'HOP102', characterized by its compact and upright to outwardly spreading and uniformly mounding plant habit; vigorous growth habit; freely branching habit; dark green-colored leaves; freely flowering habit with numerous purplish red-colored flowers that resist fading; and resistance to *Stemphylium* Leaf Spot.

2 Drawing Sheets

Figure 2:
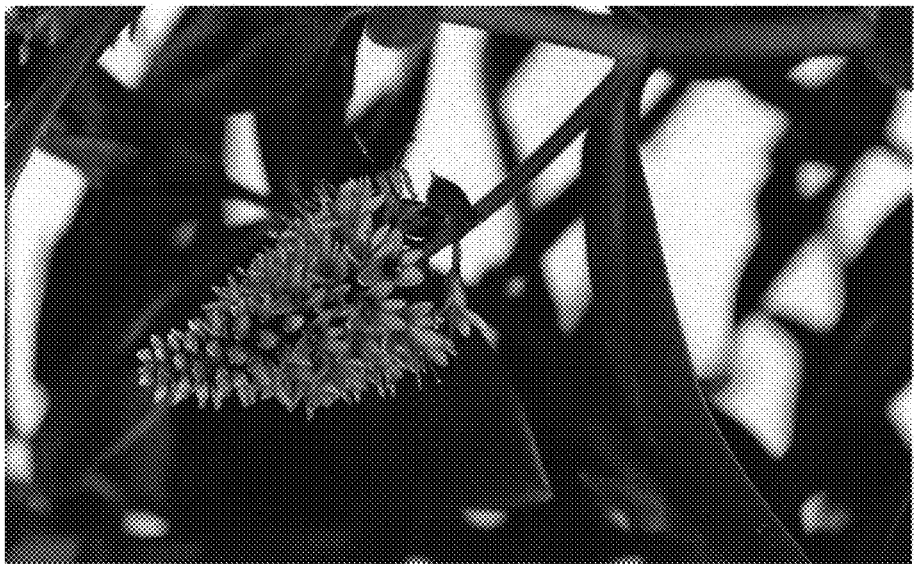

Botanical designation: *Hebe* Comm. ex. Juss.
Cultivar denomination: 'HOP102'.

STATEMENT REGARDING PRIOR DISCLOSURES BY THE INVENTOR & APPLICANT/ASSIGNEE

An European Community Plant Breeder's Rights application for the instant plant was filed by the Applicant/Assignee, Firma E. Hopmans of Wieringerwerf, The Netherlands on Feb. 6, 2020, application number 2020/0419. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hebe* plant, botanically known as *Hebe* Comm. ex. Juss, typically grown as a potted plant and hereinafter referred to by the name 'HOP102'.

The new *Hebe* plant is a product of a planned breeding program conducted by the Inventor in Wieringerwerf, The Netherlands. The objective of the breeding program is to create new compact *Hebe* plants with dark-colored leaves and numerous attractive flowers.

The new *Hebe* plant originated from a cross-pollination in April, 2015 of a proprietary selection of *Hebe* Comm. ex. Juss. identified as code number 279A, not patented, as the female, or seed, parent with a proprietary selection of *Hebe* Comm. ex. Juss. identified as code number 318B, not patented, as the male, or pollen, parent. The new *Hebe* plant was discovered and selected by the Inventor as a single flowering plant from within the progeny of the stated cross-pollination in a controlled greenhouse environment in Wieringerwerf, The Netherlands in October, 2015.

Asexual reproduction of the new *Hebe* plant by terminal stein cuttings in a controlled greenhouse environment in Wieringerwerf, The Netherlands, since February, 2016 has shown that the unique features of this new *Hebe* plant are stable and reproduced true to type in successive generations.

SUMMARY OF THE INVENTION

Plants of the new *Hebe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HOP102'. These characteristics in combination distinguish 'HOP102' as a new and distinct *Hebe* plant:

1. Compact and upright to outwardly spreading and uniformly mounding plant habit.
2. Vigorous growth habit.
3. Freely branching habit.
4. Dark green-colored leaves.
5. Freely flowering habit with numerous purplish red-colored flowers that resist fading.
6. Resistance to *Stemphylium* Leaf Spot.

Plants of the new *Hebe* differ primarily from plants of the female parent selection in flower color as plants of the new *Hebe* have purplish red-colored flowers whereas plants of the female parent selection have blue-colored flowers. In addition, plants of the new *Hebe* have smaller leaves than plants of the female parent selection.

Plants of the new *Hebe* differ primarily from plants of the male parent selection in flower color as plants of the new *Hebe* have purplish red-colored flowers whereas plants of the male parent selection have bluish purple-colored flowers. In addition, plants of the new *Hebe* are more compact than and not as upright as plants of the male parent selection.

Plants of the new *Hebe* can be compared to plants of *Hebe* Comm. ex. Juss. 'Zita', not patented. In side-by-side comparisons, plants of the new *Hebe* differ primarily from plants of 'Zita' in inflorescence length as plants of the new *Hebe* have shorter inflorescences than plants of 'Zita'. In addition, plants of the new *Hebe* are more compact than and not as upright as plants of 'Zita'.

BRIEF DESCRIPTION OF THE PHOTOGRAPHS

The accompanying colored photographs illustrate the overall appearance of the *Hebe* plant showing the colors as true as it is reasonably possible to obtain in colored reproductions of this type. Colors in the photographs may differ slightly from the color values cited in the detailed botanical description which accurately describe the actual colors of the new *Hebe* plant.

Figure 1:
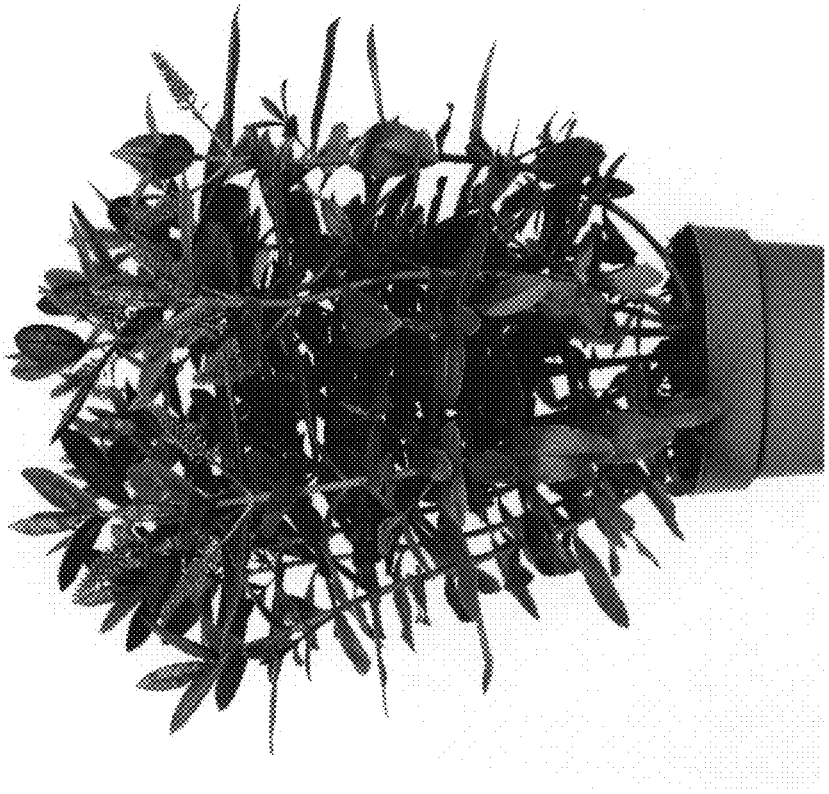

The photograph at the left of the first sheet (FIG. 1) comprises a side perspective view of a typical flowering plant of 'HOP102' grown in a container.

The photograph at the right of the first sheet (FIG. 2) is a close-up view of typical leaves and an inflorescence.

Figure 3:
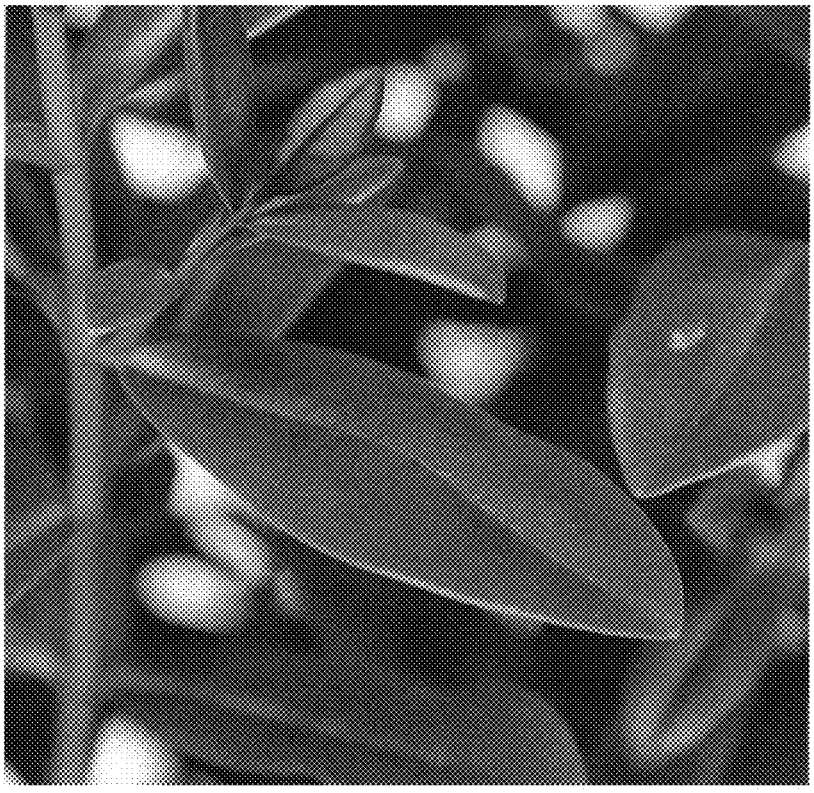

The photograph at the top of the second sheet (FIG. 3) comprises a side perspective view of a typical lateral branch and leaves of 'HOP102'.

Figure 4:
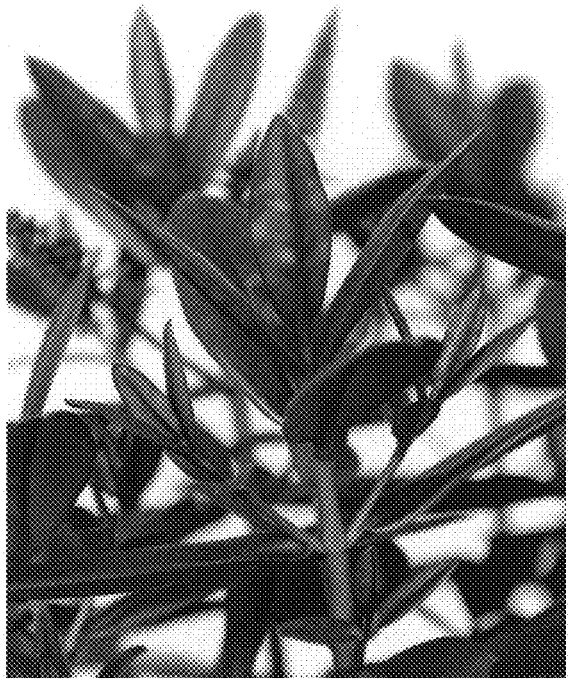

The photograph at the bottom of the second sheet (FIG. 4) is a close-up view of typical developing leaves of 'HOP102'.

DETAILED BOTANICAL DESCRIPTION

Plants used for the aforementioned photographs and following description were grown with two plants per 15-cm containers during the autumn initially in a glass-covered greenhouse and finished in a outdoor nursery in Wieringerwerf, The Netherlands and under cultural practices typical of commercial *Hebe* production. During the production of the plants, day temperatures ranged from 16° C. to 20° C. and night temperatures ranged from 12° C. to 16° C. Plants were pinched one time about one month after planting and were six months old when the photographs and the description were taken. In the following description, color references are made to The Royal Horticultural Society Colour Chart, 2015 Edition, except where general terms of ordinary dictionary significance are used.

Botanical classification: *Hebe* Comm. ex. Juss. 'HOP102'.

Parentage:

- *Female, or seed, parent.*—Proprietary selection of *Hebe* Comm. ex. Juss. identified as code number 279A, not patented.
- *Male, or pollen, parent.*—Proprietary selection of *Hebe* Comm. ex. Juss. identified as code number 318B, not patented.

Propagation:

- *Type cutting.*—Terminal stein cuttings.
- *Time to initiate roots, summer.*—About ten days at temperatures about 18° C.
- *Time to initiate roots, winter.*—About 14 days at temperatures about 20° C.
- *Time to produce a rooted young plant, summer.*—About 40 days at temperatures about 18° C.
- *Time to produce a rooted young plant, winter.*—About 50 days at temperatures about 20° C.
- *Root description.*—Medium in thickness, fleshy; typically white to brown in color, actual color of the roots is dependent on substrate composition, water quality, fertilizer type and formulation, substrate temperature and physiological age of roots.
- *Rooting habit.*—Moderately freely branching; medium dense.

Plant description:

- *Plant type.*—Evergreen perennial shrub.
- *Plant and growth habit.*—Compact and upright to outwardly spreading and uniformly mounding plant habit; vigorous to vigorous growth habit and moderate to rapid growth rate.
- *Plant height, soil level to top of foliar plane.*—About 38.1 cm.
- *Plant height, soil level to top of floral plane.*—About 36.1 cm.
- *Plant width.*—About 42.2 cm.
- *Lateral branch description.*—Branching habit: Freely branching habit with about four primary branches, each with about six secondary branches; pinching will enhance lateral branching. Length (excluding inflorescence): About 13.2 cm. Diameter: About 3 mm. Internode length: About 2.1 cm. Strength: Strong. Aspect: Erect to about 45° from vertical. Texture and luster: Mostly smooth and glabrous; at the internodes, moderately pubescent; moderately glossy. Color, developing: Close to 144A and 146A. Color, developed: Close to 144B; at the internodes, close to 146C.

Leaf description:

- *Arrangement.*—Opposite, simple.
- *Length.*—About 6.7 cm.
- *Width.*—About 3 cm.
- *Shape.*—Elliptic to slightly obovate.
- *Apex.*—Broadly apiculate with a blunt acute tip.
- *Base.*—Cuneate.
- *Margin.*—Entire; slightly revolute and slightly and coarsely undulate.
- *Texture and luster, upper surface.*—Smooth, glabrous; not rugose; moderately glossy.
- *Texture and luster, lower surface.*—Smooth, glabrous; not rugose; slightly glossy.
- *Venation pattern.*—Pinnate.
- *Color.*—Developing leaves, upper surface: Close to 143A; midvein, close to 183A. Developing leaves, lower surface: Close to 148A; towards the margins, slightly tinged with close to 187A; midvein, close to 187A. Fully expanded leaves, upper surface: Slightly darker than NN137A; venation, close to N148A and N148B. Fully expanded leaves, lower surface: Close to a blend of 146A and 146B; venation, close to 148B.

*Petioles: Length: About* 2.75 mm. Diameter: About 2 mm by 4.5 mm. Strength: Strong. Texture and luster, upper and lower surfaces: Smooth, glabrous; slightly glossy. Color, upper surface: Close to 152C and 152D; at the margins, close to N77A to lighter than N77A. Color, lower surface: Close to 145A.

Flower description:

*Flower arrangement and shape.*—Single campanulate flowers arranged on dense axillary racemes; flowers face mostly outwardly.

*Flowering habit.*—Freely flowering habit with about 95 flowers developing per inflorescence and about 1,400 flowers developing per plant during the flowering season.

*Fragrance.*—None detected.

*Natural flowering season.*—Plants flower continuously from the summer into the autumn in The Netherlands.

*Flower longevity.*—Flowers last about one week on the plant; flowers not persistent.

*Flower buds.*—Length: About 5 mm. Diameter: About 2 mm. Shape: Oblong, slightly curved. Texture and luster: Smooth, glabrous; matte. Color: Developing sepals, close to 138C; developing petals, close to 64C.

*Inflorescence height* (*length*).—About 7 cm.

*Inflorescence diameter.*—About 2.3 cm.

*Flower diameter.*—About 7 mm by 7 mm.

*Flower height.*—About 8 mm.

*Throat diameter.*—About 1.5 mm.

*Tube length.*—About 3 mm.

*Tube diameter.*—About 2 mm.

*Petals.*—Quantity and arrangement: Four in a single whorl; upper petal broader than the lateral and lower petals; petals fused about 45% of the petal length from the base. Length, all petals: About 7 mm. Width, upper petal: About 2 mm. Width, lateral petals: About 1.5 mm. Width, lower petal: About 1 mm. Shape, all petals: Narrowly obovate. Apex, upper petal: Bluntly acute. Apex, lateral and lower petals: Acute. Margin, all petals: Entire; not undulate. Texture and luster, all petals, upper and lower surfaces: Smooth, glabrous; slightly glossy. Texture and luster, throat and tube: Smooth, glabrous; slightly glossy. Color, all petals: When opening, upper surface: Close to 61C. When opening, lower surface: Close to 64B to 64C. Fully opened, upper surface: Close to 61C; venation, close to 72B; color does not change with subsequent development. Fully opened, lower surface: Close to 64C; venation, close to 64C; color does not change with subsequent development. Throat: Close to 71C; venation, close to 71C. Tube: Close to a 72B; venation, close 72B.

*Sepals.*—Quantity and arrangement: Four arranged in a single whorl and fused at the base. Length: About 2.5 mm. Width: About 1.25 mm. Shape: Narrowly ovate. Apex: Acute. Base: Cuneate, fused. Margin: Entire. Texture and luster, upper and lower surfaces: Smooth, glabrous; matte. Color: When opening, upper surface: Close to 138C. When opening, lower surface: Close to 138B. Fully opened, upper and lower surfaces: Close to 138B.

*Peduncles.*—Length: About 6.6 cm. Diameter: About 1.75 mm. Aspect: Upright to about 45° from stein axis. Strength: Strong. Texture and luster: Densely pubescent; slightly glossy. Color: Close to 143B.

*Pedicels.*—Length: About 3 mm. Diameter: About 0.5 mm. Aspect: About 45° from peduncle axis. Strength: Moderately strong. Texture and luster: Densely pubescent; matte. Color: Close to 143B.

*Flower bracts.*—Quantity and arrangement: One at the base of each flower. Length: About 3 mm. Width: About 1 mm. Shape: Narrowly ovate. Apex: Acute. Base: Cuneate. Margin: Entire. Texture, upper and lower surfaces: Smooth, glabrous. Color, upper and lower surfaces: Close to 137B.

*Reproductive organs.*—Stamens: Quantity per flower: Two. Filament length: About 7 mm. Filament color: Close to 64C; proximally, close to 70B. Anther size: About 0.5 mm by 1 mm. Anther shape: Oblong. Anther color: Close to 61A. Pollen amount: Moderate. Pollen color: Close to 155D. Pistils: Quantity per flower: One. Pistil length: About 8 mm. Stigma diameter: About 3 mm. Stigma shape: Club-shaped. Stigma color: Greyish white. Style length: About 7.97 mm. Style color: Close to 77A. Ovary color: Close to a 143B.

*Seeds and fruits.*—To date, seed and fruit development has not been observed on plants of the new *Hebe*.

Pathogen & pest resistance: Plants of the new *Hebe* have exhibited resistance to *Stemphylium* Leaf Spot. To date, plants of the new *Hebe* have not been noted to be resistant to pests and other pathogens common to *Hebe* plants.

Garden performance: Plants of the new *Hebe* have exhibited good garden performance and to be tolerant to rain, wind, temperatures ranging from about −7° C. to about 40° C. and to be suitable for USDA Hardiness Zones 8 through 11.

It is claimed:

1. A new and distinct *Hebe* plant named 'HOP102' as illustrated and described.

* * * * *